(12) United States Patent
Ash (10) Patent No.: US 6,958,049 B1
(45) Date of Patent: Oct. 25, 2005

(54) METHOD OF ENHANCING CATHETER PATENCY USING A CITRATE SALT CATHETER LOCK SOLUTION

(75) Inventor: Stephen R. Ash, Lafayette, IN (US)

(73) Assignee: Ash Access Technology, Inc., Lafayette, IN (US)

( * ) Notice: Subject to any disclaimer, the term of this patent is extended or adjusted under 35 U.S.C. 154(b) by 0 days.

(21) Appl. No.: 09/763,666

(22) PCT Filed: Aug. 25, 1999

(86) PCT No.: PCT/US99/19307
§ 371 (c)(1),
(2), (4) Date: May 25, 2001

(87) PCT Pub. No.: WO00/10385
PCT Pub. Date: Mar. 2, 2000

Related U.S. Application Data
(60) Provisional application No. 60/097,777, filed on Aug. 25, 1998.

(51) Int. Cl.$^7$ ............................................. A61M 1/00
(52) U.S. Cl. ...................................... 604/28; 514/574
(58) Field of Search ........................... 604/28, 29, 30; 514/574

(56) References Cited

U.S. PATENT DOCUMENTS

| | | | |
|---|---|---|---|
| 4,364,929 A | 12/1982 | Sasmor et al. ................ 424/80 |
| 4,677,143 A | 6/1987 | Laurin et al. ................ 523/122 |
| 5,032,615 A | 7/1991 | Ward et al. .................. 514/574 |
| 5,109,025 A | * 4/1992 | Satoh et al. ................. 514/679 |
| 5,665,061 A | 9/1997 | Antwiler ........................ 604/4 |
| 5,688,516 A | 11/1997 | Raad et al. |
| 5,709,993 A | 1/1998 | Buturovic-Ponikvar ........ 435/2 |
| 5,843,016 A | 12/1998 | Lugnani et al. ............... 604/21 |
| 6,166,007 A | * 12/2000 | Sodemann ............... 514/222.5 |
| 6,190,371 B1 | * 2/2001 | Maginot et al. ............. 604/523 |
| 6,423,050 B1 | 7/2002 | Twardowski |
| 6,423,706 B2 | 7/2002 | Sodemann |
| 6,451,003 B1 | 9/2002 | Prosl et al. |

OTHER PUBLICATIONS

Olinger GN, Hottenrott C, Mulder DG, Maloney JV, Miller J, Patterson RW, Sullivan SF, Buckberg GD. Acute clinical hypocalcemic myocardial depression during rapid blood transfusion and postoperative hemodialysis. *Journal of Thoracic and Cardiovascular Surgery* 72: 503–511, Oct. 1976.

Dzik WH, Kirkley SP. Citrate toxicity during massive blood transfusion. *Transfusion Medicine Reviews* 2:76–94, Jun. 1988.

Kelleher SP, Schulman G. Severe metabolic alkalosis complicating regional citrate hemodialysis. *Am J Kidney Dis* 9: 235–236, Mar. 1987.

Lohr JW, Slusher S, Diederich D. Safety of regional citrate hemodialysis in acute renal failure. *Am J Kidney Dis* 8:104–107, Feb. 1989.

Leray–Moragues H, Bose LY, Canaud B. Gentamicin/sodium citrate mixture: a promising antibiotic lock for preventing catheter related infections. Lapeyronie Univerity Hospital, Montpellier, France.

Von Brecht JH, Flanigan MJ, Freeman RM, Lim VS. Regional anticoagulation: hemodialysis with hypertonic trisodium citrate. *Am J Kidney Dis* 8:196–201, Sep. 1986.

Purchase L, Gault MH. Hemodialysis with a Permcath kept open with streptokinase and later citrate in a heparin–sensitive patient. *Nephron* 48:119–120, 1991.

Flanigan MJ, Pillsbury L, Sadewasser G, Lim VS. Regional hemodialysis anticoagulation: hypertonic tri–sodium citrate or anticoagulant citrate dextrose–A. *Am J Kidney Dis* 27:519–524, Apr. 1996.

Sodemann K, Lubrich–Birkner I, Berger O, Baumert J, Feldmer B, Von Hodenberg E Gentamicin/sodium–citrate mixture as antibiotic–lock technique for salvage and prevention of catheter–related infections—A four year trial. *J Am Soc Nephrol* 8: 173A, 1997.

Buturovic J, Ponikvar R, Kandus A, Boh M, Klinkmann J, Ivanovich P. Filling hemodialysis catheters in the interdialytic period: heparin versus citrate versus polygeline: a prospective randomized study. *Artif Organs* 22:945–946, 1998.

Branson PK, McCoy RA, Phillips BA, Clifton GD. Efficacy of 1.4 percent sodium citrate in maintaining arterial catheter patency in patients in a medical ICU. *Chest* 103:882–885, Mar. 1993.

Hesse A, Schreyger F., Tuschewitzki GJ, Classen A, and Bach D, Experimental investigations on dissolution of incrustations on the surface of catheters, Urologia Internationalis 1989 Switzerland, vol. 44, No. 6, 1989, pp. 364–369.

Hesse A, Nolde A, Klump B, Marklein G, and Tuschewitzki GJ, In vitro investigations into the formation and dissolution of infection–induced catheter encrustations, British Journal of Urology, vol. 70, No. 4, Oct. 1992, pp. 429–434.

\* cited by examiner

Primary Examiner—Henry Bennett
Assistant Examiner—Camtu Nguyen
(74) *Attorney, Agent, or Firm*—Woodard, Emhardt, Moriarty, McNett & Henry LLP (57) ABSTRACT

This invention relates to an infusion device for a catheter lock solution, to a method of enhancing the patency of catheters in animals and to a catheter lock solution. The device includes a syringe (34) containing a lock solution comprising a citrate salt. The method for enhancing the patency of catheters includes infusing a lumen (14, 16) of an indwelling catheter (10) with a lock solution comprising a citrate salt. In one aspect of the invention, the catheter lock solution includes a citrate salt and a viscosifying agent. The lock solution is prepared to have sufficient viscosity and density to remain in the lumen for a desired amount of time.

35 Claims, 4 Drawing Sheets

Fig. 1

METHOD OF ENHANCING CATHETER PATENCY USING A CITRATE SALT CATHETER LOCK SOLUTION

CROSS-REFERENCE TO RELATED APPLICATION

The present application claims the benefit of U.S. Provisional Application Ser. No. 60/097,777 filed on Aug. 25, 1998, which is hereby incorporated by reference in its entirety.

FIELD OF THE INVENTION

This invention generally relates to intravascular infusion devices and methods of enhancing the patency of intravascular catheters. More specifically but not exclusively, this invention relates to infusing a lock solution into an indwelling intravascular catheter and to methods of inhibiting infection in an animal having an indwelling intravascular catheter.

BACKGROUND OF THE INVENTION

Catheters are used with increasing frequency to treat patients requiring a variety of medical procedures. The catheters offer many advantages for patients; for example, catheters provide ready access without repeated injections for administration of large volumes of fluids, nutrients, medications and withdrawal of blood. The catheters can either be acute or temporary for short-term use or chronic for long-term treatment. They are commonly inserted into central veins (such as the vena cava) from peripheral vein sites. Great care must be taken in the placement and use of a chronic catheter to prevent infection of the patient at the site of access or within the vascular system. Chronic venous catheters usually contain a DACRON cuff attached to the catheter and placed under the skin, which promotes ingrowth of fibrous tissue, fixes the catheter in position, and prevents bacterial migration around the catheter.

Catheters can be used for infusion of fluids, such as, for example, drugs, electrolytes or fluids used in chemotherapy, or for the removal of blood on an intermittent basis. For example, in hyperalimentation treatment, the catheters are usually used for infusion of large volumes of fluids. In chemotherapy, catheters are used for infusion of drugs on an intermittent basis, ranging from daily to weekly. For hemodialysis, dual-lumen catheters are used—usually three times per week; one lumen allows removal of blood, while the other lumen allows blood to return. However, catheters, especially chronic catheters, have drawbacks. They can become occluded by a thrombus, and even if extreme care is taken, the catheters can increase a patent's risk of infection.

In order to prevent clotting of the catheters between uses, the catheters are usually filled with a lock solution that comprises a concentrated solution of the commonly used anticoagulant, heparin (up to 10,000 units of heparin per catheter lumen). The heparin lock solution is injected into each lumen immediately after each use, and preferably left in the catheter until the catheter is accessed again. The heparin lock solution must be withdrawn from the catheter before the next use because infusing this amount of heparin in a patient might result in excessive bleeding.

However, even with the use of a heparin lock solution, the catheter can become occluded between uses from coagulation of blood in the catheter. Blood may be found in the catheter because, for example, an inadequate volume of heparin was infused within the catheter lumen, the heparin diffused from the lumen, or residual blood remains in the lumen. This often results in formation of a thrombus with concomitant loss of flow through the lumen. The occluded catheters frequently are removed and/or replaced.

Since catheters are inserted into veins or arteries, they bypass the protective dermis layer, and provide direct access to a patient's blood stream. This can cause the inadvertent transfer of infectious agents into the vein or artery at the location of the catheter. In addition, the foreign surfaces of catheters can create a smooth surface at which bacteria can grow, and at which the white cells are unable to surround or "phagocytize"the bacteria.

Heparin has no anti-bacterial properties and, in fact, may help to promote growth of bacteria within the "biofilm" layer of protein on the catheter surfaces (protamine has the opposite effect). The "biofilm" proteins on the catheter surfaces can protect bacteria from antibiotics and white cells. Also, heparin induces the loss of platelets and, paradoxically, can induce clotting in some patients (the "white clot" syndrome). Since catheters, particularly venous catheters, are frequently accessed with syringes, or uncapped and directly connected to IV lines, they have a propensity to become contaminated. If there is bacteremia (bacteria in blood), then the catheter surfaces within the vein or artery can become seeded with bacteria. In either case, the patient can develop septicemia (infection in the blood) and become seriously ill. Often these patients must be hospitalized and given intravenous antibiotics. In spite of this care, patients often remain seriously ill until the infected catheter is removed.

Thus in light of the above described problems, there is a continuing need for advancements in the relevant field, including improved methods, composition and devices relating to enhancing the patency of indwelling intravascular catheters. The present invention is such an advancement and provides a wide variety of benefits and advantages.

SUMMARY OF THE INVENTION

The present invention relates to catheter lock solutiona, intravascular infusion devices for infusing a lock solution into patient and to methods for enhancing the patency of intravascular catheters. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

In one form, the present invention provides a method of treating patients having an indwelling intravascular catheter. The method comprises selecting a patient having an indwelling intravascular catheter defining a lumen therethrough and having an infection or a substantial risk of infection related to the presence of the catheter; and infusing a catheter lock solution into the lumen. The solution comprises a citrate salt solution having a concentration effective to eliminate infection and to reduce the likelihood of subsequent infection. In one embodiment, the citrate salt can be included in the catheter lock solution in a concentration preferably within the range, in weight percent, of about 1.5% to about 50%. The catheter lock solution can include a viscosifying agent such as polyethylene glycol, glycerin, polyglycerin or mixtures thereof. In an alternative embodiment, the lock solution is prepared to have a pH level lower than about 6.5, more preferably between about 4.5 and about 6.5.

In another form, the present invention includes a method of inhibiting infections in an animal having an indwelling catheter defining a lumen therethrough. The method comprises infusing into the lumen a pharmaceutically acceptable lock solution including a compound having anticoagulant and antibiotic activity. The lock solution has a density and a viscosity sufficient to maintain the lock solution in the lumen for a desired amount of time. Preferably the lock solution has a viscosity of from about 1.5 cP to about 4.0 cP. In one embodiment the lock solution includes the citrate salt in a hypertonic concentration, preferably in a concentration between about 1.5 and about 6.5. In another embodiment the lumen of the catheter has an internal volume and a sufficient amount of the lock solution is infused into the lumen, to fill, in percent by volume, between about 80% and about 100% of the internal volume of the lumen.

In yet another form, the present invention provides a method of treating animals that exhibit a risk of infection and having a surgically implanted catheter. The method comprises adding a pharmaceutically acceptable lock solution comprising a bactericidal component into the catheter. The bactericidal component includes greater than about 50 wt %, based on the weight of the bactericidal component, of a citrate salt. In preferred embodiments, the pharmaceutically acceptable lock solution is prepared to be sufficiently caustic to substantially inhibit the growth of bacteria and microorganisms in the lumen.

In still yet another form, the present invention includes an infusion device for infusing a lock solution into a lumen of a catheter. The infusion device includes a syringe and a catheter lock solution contained in the syringe. The lock solution is preferably a pharmaceutically acceptable solution comprising a citrate salt, and the syringe containing the solution is preferably sterilized. The solution may also include a viscosifying agent to provide to the lock solution sufficient viscosity and density to remain in the lumen for a desired amount of time. In preferred embodiments, the lock solution has a density of between about 1.0 g/ml and about 1.5 g/ml and a viscosity between about ⅕ cP and about 4.0 cP.

In still another form, the present invention provides a kit for accessing a patient's intravascular system. The kit comprises: a catheter defining therethrough at least one lumen; a container; and a catheter lock solution contained within the container, the solution comprising a citrate salt solution.

In yet another from, the present invention provides a catheter lock solution. The lock solution includes, in weight percent, about 1.5% to about 50% of a citrate salt, and an amount of a viscosifying agent sufficient provide the lock solution with a viscosity of from about 1.0 cP to about 4.0 cP.

Further objects, features, aspects, forms, advantages and benefits shall become apparent from the description and drawings contained herein.

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

In one form, the present invention provides a catheter having retained therein a lock solution. The lock solution enhances the patency of the catheter and exhibits anticoagulation and antibiotic activity. The lock solution provides particular advantages by increasing the longevity of catheters, reducing incidence of catheter occlusion, and reducing incidence of sepsis or bacterial infection in the patient. In addition, the lock solution of the present invention can be used with or without other anticoagulant agents and/or other antibacterial agents. Further, certain lock solutions of the present invention can be infused into the patient from the catheter in preparation for a subsequent use of the catheter without the necessity of withdrawing the lock solution from the catheter before infusion of additional fluids or medications.

In another form, the present invention provides a method of enhancing the patency of a catheter. The method includes infusing into the catheter a lock solution selected in accordance with the invention and allowing the lock solution to remain in the catheter for a desired amount of time between catheter uses.

The catheters for use with the present invention typically can either be acute (temporary) or chronic (long-term) catheters surgically implanted in the animal. The catheters usually are inserted into a vein or artery. The catheters are typically used in varying intervals to administer fluids, nutrients, and medications into the body. The catheters also can be used to withdraw body fluids, such as blood, for hemodialysis treatment. When not in use, the catheter remains in its intravascular position until subsequent treatment is preferred.

The catheters used accordance with this invention include known and commonly used catheters and are readily available from a variety of commercial sources. The catheters may vary in configuration and size. One type of catheter commonly used in accordance with this invention is a tunneled catheter that includes a cuff for ingrowth of tissue to anchor the catheter. Examples of catheters that may be used include, but are not restricted to, an ASH SPLITCATH by Ash Medical of West Lafayette, Ind.; TESIO and ASH CATHETERS by Medcomp of Harleysville, Pa.; PERM CATH by Quinton Instrument Company of Seattle, Wash.; HICKMAN and VAS CATH by Bard, Inc. of Salt Lake City, Utah. Catheters containing totally subcutaneous ports are also useful in the present invention; examples include LIFESITE by Vasca of Topsfield, Me., and DIALOCK by Biolink, Inc. of Boston, Mass.

Figure 1:
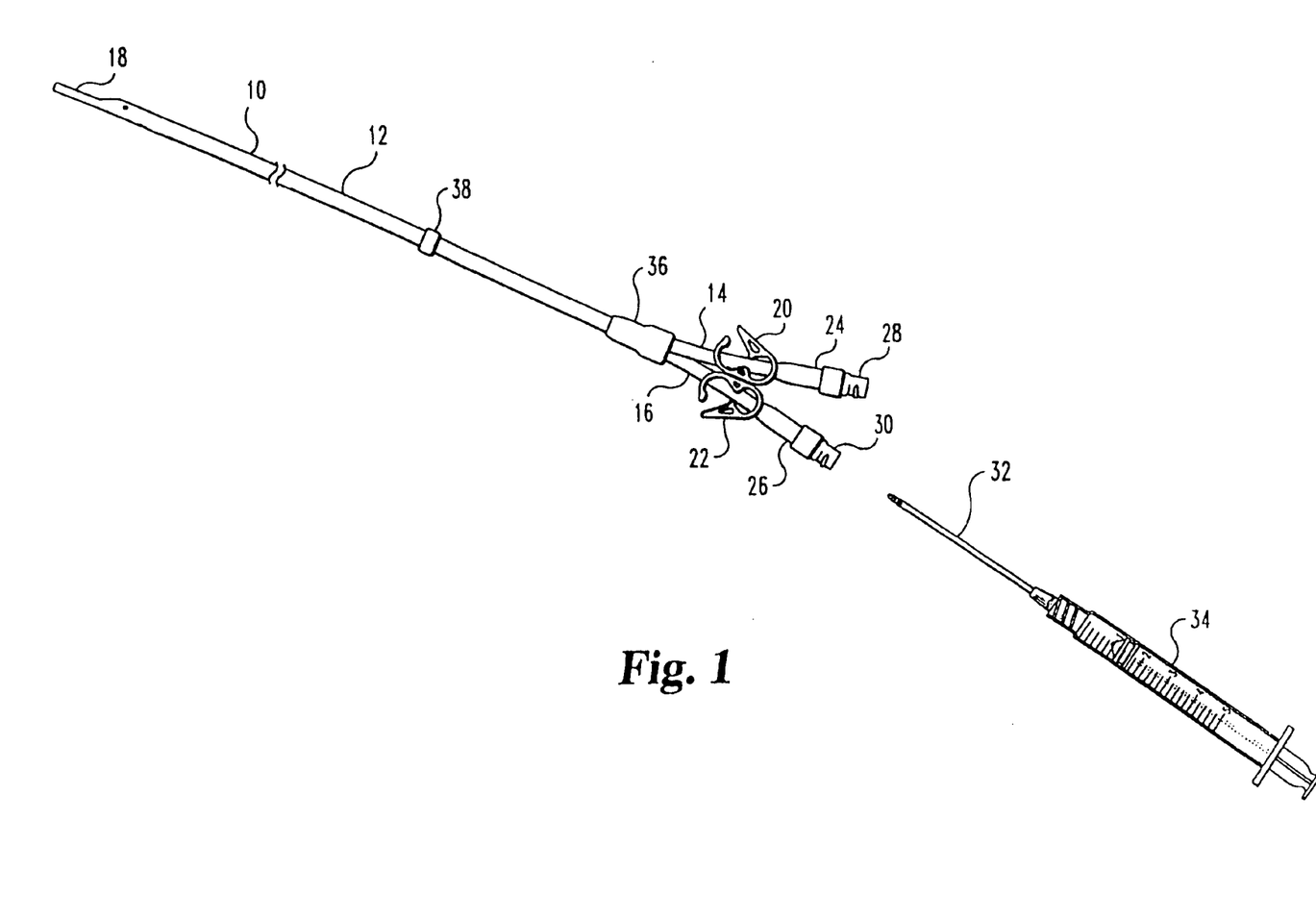
FIG. 1 is a perspective view of one embodiment of a catheter and syringe for infusing a lock solution into a catheter for use with the present invention.

FIG. 1 depicts one example of a catheter 10 for use with this invention. Catheter 10 is a dual lumen catheter and includes an outer sheath 12 having a cuff 38 and first and second lumens 14 and 16, respectively. Lumens 14 and 16 extend from distal tip 18 through sheath 12 and exit from sheath 12 at connection 36. Each of lumens 14 and 16 include releasable clamps 20 and 22, respectively. Each of lumens 14 and 16 terminate in a threaded end 24 and 26, which can be threadedly attached to protective end caps 28 and 30, respectively. Fluids including a lock solution can be infused or withdrawn from each lumen 14 and 16 by inserting needle 32 of a syringe 34 through protective end caps 28 and/or 30 after protective end caps 28 and/or 30 have been sterilized by cleaning successively, for example with betadine and alcohol. Alternatively, one or both protective end caps 28 and 30 can be removed and threaded ends 24 and 26 can be threadedly attached via a connector (not shown) to lines for infusion or withdrawal of fluids (not shown). Once a desired treatment session has been completed, the needles are removed or the connectors are replaced with fresh, sterile protective end caps. The lumens are then typically flushed with normal saline, after which a lock solution is injected into each lumen. All procedures are performed using standard sterile techniques well known to those skilled in the art. The catheters for use with this invention can be prepared from a variety of materials, including, for example, silicon, polyurethane, polyvinyl, silicone, or silastic elastomer.

Chronic catheters are usually inserted through an internal jugular vein into the superior vena cava. Usually these catheters include a cuff attached to the exterior of the catheter and placed under the skin, which promotes ingrowth of fibrous tissue, and thus fixes the catheter in position and prevents bacterial migration around the catheter. While the catheters are manufactured to function for several months, for example, TESIO catheters can last for up to four years with proper intervention, in actual practice, the catheters, prior to the present invention, have exhibited limited longevity because of occlusion and/or infection. These catheters frequently must then be removed and/or replaced.

As mentioned above, in order to prevent clotting of catheters between use, catheters are commonly filled with lock solutions comprising an anticoagulant agent and sometimes a second agent having antibacterial properties. It has unexpectedly been determined that citrate salt solutions as described herein exhibit surprisingly effective antibacterial activity. In a series of tests, with a variety of bacterium spores injected into a 47% solution of citrate salts, a six-log kill is obtained in seven days for *E. coli* and *P. aeruginosa*, and in 21 days for *S. Aureus*.

In accordance with the invention a catheter lock solution comprising a citrate salt is used to increase the patency of implanted catheters. As used herein, the term "lock solution" refers to a solution that is injected or otherwise infused into a lumen of a catheter and with the intention of allowing a substantial portion of a lock solution to remain in the lumen until it is desired or required to access that particular lumen again, typically for additional treatment, i.e., infusion or withdrawal of fluid. Preferably the lock solution can remain in the lumen for a desired amount of time lasting from about 1 hour to 3 or 4 days or longer. However, frequently the lock solution is changed on a daily basis during regular care and sterile maintenance of the indwelling catheter. Use of a lock solution of the present invention provides particular advantages for patients with catheters by prolonging the lifetime of the catheter, lengthening the interval between required replacements of the lock solution and inhibiting infections in the patient.

In one form, the lock solution of the present invention comprises an amount of a citrate salt to provide an effective catheter lock solution, preferably, but not exclusively, a hypertonic lock solution. The term hypertonic is used herein to refer to a fluid having an osmotic concentration and a density greater than the osmotic concentration and density of the blood of the patient. The lock solution preferably comprises a citrate salt with a concentration range, in weight percent, of from about 1.5% to about 50% with an osmolality of about 300 to about 6400 mOsm. More preferably, the lock solution comprises citrate salt in a concentration range of from about 10% to about 40%, yet more preferably, in a concentration range of from about 20% to about 30%.

In preferred embodiments, the lock solution comprises a citrate salt, and the lock solution is prepared to have sufficient viscosity and density to remain in the lumen for a desired amount of time. It is well known that catheters are manufactured to have a variety of configurations and lumen diameters. For example, catheters can include single or double lumens. The double lumens can be fused adjacent to each other or they can be concentric. The lumens can have varying cross-sectional areas and shapes, ranging from substantially circular to substantially ovoid. A phenomenon common to most lock solutions is that a portion of the solution at the distal end of the lumen diffuses into the patient's blood stream and is replaced in the catheter by blood. While not intending to be bound by any theory, it is thought that the rate of diffusion of a lock solution from a lumen can be influenced by the cross-sectional shape and area of the particular lumen(s), the density of the lock solution, and the viscosity of the lock solution. Typically, high density lock solutions tend to fall out of the lumen of the catheter, allowing blood to enter into the lumen.

A lock solution of the present invention is preferably prepared to have a viscosity and density such that a substantial portion of the lock solution does not diffuse or flow out of a catheter lumen within about 8 hours. More preferably, the lock solution of the present invention does not diffuse out of a lumen to a substantial extent within about 12 hours, still more preferably within about 24 hours.

In a preferred aspect of the invention, the lock solution of the invention is prepared to have a selected density of from about 1.02 g/ml to about 1.04 g/ml and a viscosity of from about 1.5 centipoise (cP) to about 4.0 cP. More preferably the lock solution has a density of from about 1.02 g/ml to about 1.03 g/ml and a viscosity of from about 1.5 cP to about 2.0 cP. For example in a 10 French TESIO catheter studies with sodium citrate solutions, 46.7% by weight citrate with density of 1.025 and viscosity of 2.0 (by gravity viscometer) where found to remain within the cylindrical catheter for 3 days or more, with the catheter suspended in a solution having viscosity of blood, 13 cP at 37°. In catheters such as the SPLITCATH, with lumens having less hydraulic resistance, this solution will exit the catheter due to gravitational forces. A catheter lock solution comprising 23% by weight citrate, however, will remain in place for 3 days or more.

The density of the lock solution can be varied by varying the amount of salts included in the solution, with 46.7% being appropriate for 10 French cylindrical catheters, and 23% being appropriate for the double-D shaped lumens of the SPLITCATH.

The viscosity of the lock solution can be varied by adding a viscosifying agent. Viscosifying agents useful with the present invention include those pharmaceutically acceptable agents known or commonly used in treatment of animals including humans. Examples include, but are not limited to, polyethylene glycol, glycerin, polygeline, and non-metabolizable sugars such as sorbitol and mannitol and mixtures of these compounds. An excellent aspect of the invention, therefore is a composition useful as a lock solution that comprises a citrate salt and a viscosifying agent. The viscosifying agent allows higher concentration of citrate to be used without having egress of the lock solution from the catheter due to high density of the lock solution.

While is understood that optimal viscosity and density are dependent upon the shape and size of a particular lumen, a person of ordinary skill in the art, in view of the description herein, can readily determine a desired density and viscosity for a particular catheter without undue experimentation.

In a preferred embodiment, the lock solution is prepared to have a pH lower than that of the pH of the patient's blood. For example, in humans, the lock solution may advantageously be prepared to have a pH lower than about 6.5, more preferably, the lock solution is prepared to have a pH level of from about 4.5 to about 6.5. Still yet more preferable, the lock solution is prepared to have a pH level of from about 5.0 to about 6.5. The lower the pH, the greater the antibacterial effect of the citrate and the greater the caustic activity in dissolving clots. The pH of the catheter lock solution can be varied by adding either an acid or base according to methods known to those skilled in the art. For example, the pH of the catheter lock solution can be lowered by including a sufficient amount of citric acid to the solution to provide the desired pH level.

An inventive lock solution can be prepared to include a variety of other pharmaceutically acceptable agents. For example, the lock solution can include salts, such as, for example, sodium chloride and sodium heparin. The lock solution can also include a variety of other antibacterial, antimicrobial and anticoagulant agents. Such antibacterial and antimicrobial agents are well known to those skilled in the art and can include, without limitation, gentamicin, vancomycin, and mixtures of these agents. Additional anticoagulant agents include, for example heparin, urokinase, tissue plasminogen activation (tPA) and mixtures of these agents.

By "pharmaceutically acceptable", it is meant that the lock solution and the included salts and other additives which are, within the scope of sound medical judgment, suitable for use in contact with tissues of humans and lower animals without undue toxicity, irritation, allergic response, and the like, and are commensurate with the reasonable benefit/risk ratio. It is also typically necessary that a composition be sterilized to reduce the risk of infection. For example, pharmaceutically acceptable salts are well-known in the art, for example, as found in S. M. Berge et al. described in detail in *J. Pharmaceutical Science*, 66:1–19, 1977.

In yet another form, the present invention provides a method of inhibiting infections in animals having an indwelling intravascular catheter. A compound having anticoagulant and antibacterial activity is selected, for example, the citrate salt such as trisodium citrate. A lock solution is prepared, including the compound having anticoagulant and antibacterial activity. The resulting lock solution is then infused into the lumen or a catheter.

Thus, the lock solution of the present invention including a citrate salt can be prepared and further include a bactericidal component. In a preferred embodiment, the bactericidal component includes greater than 50% by weight based on the weight of the bactericidal component of the citrate salt. More preferably, the bactericidal component includes greater than about 75%, by weight based on the weight of the component, of the citrate salt. Still more preferably, the bactericidal component includes greater than about 90% of a citrate salt.

Once a lock solution is infused into the lumen of the catheter, it is allowed to remain until that particular catheter or lumen is desired to be accessed again. The lock solution can be flushed directly into the patient without the necessity of removing the fluid before infusing fluids for subsequent treatment. Alternatively, the lock solution can be removed from the catheter prior to infusion or removal of additional fluid for further treatment.

When the lock solution of the present invention is injected into the lumen of the catheter, a sufficient amount of the lock solution can be injected to substantially fill the lumen of the catheter. Alternatively, a volume less than the amount of fluid needed to fill the catheter can be injected into the lumen. For example, a sufficient amount of lock solution can be injected into the catheter to fill about 80 to about 100% of the internal volume of the catheter. In yet another embodiment, an amount greater than the internal volume of the catheter can be injected. For example, an amount of the lock solution greater than or equal to about 1.1 times the internal volume of the catheter can be injected into the lumen, without adverse effects on the clotting system of the patient.

In yet another embodiment, the lock solution of the present invention can be infused into the lumen or lumens of the indwelling catheter of patients exhibiting a risk of infection. Surgically implanted catheters are used in the treatment of patients exhibiting a variety of health problems. It is well known that certain health problems and/or patients exhibit increased risk of infection based upon historical observation by those skilled in the art. The present invention provides distinct advantages when used on those patients having an increased risk of infection by inhibiting infection in those patients.

In another embodiment, patients are screened for an infection or a substantial risk of infection related to the presence of the catheter. For those patients having such an infection or substantial risk of infection, a catheter lock solution prepared according to the present invention is infused into the lumen of the catheter. The catheter lock includes a citrate salt in a concentration effective to eliminate the infection and/or reduce the likelihood of subsequent infection.

A lock solution of the present invention has other advantages besides antibacterial properties. If infused into a patient, citrate in the lock solution will be inactivated by calcium in the blood or calcium derived from body stores. When a lock solution having a hypertonic citrate concentration of 47% is used, the total amount of citrate in the lock solution contained in one lumen of a tunneled catheter is approximately 2 ml, containing 3.4 mM of sodium citrate. This amount of citrate is equal to the amount of calcium contained in 1.5 liters of blood. If infused rapidly, this amount of citrate could cause transient hypocalcemic symptoms, but would not anticoagulate the patient. Therefore, if a tunneled catheter is used for fluid infusion for a patient in the. emergency room or operating room, the patient will not become anticoagulated just at the time when blood coagulation is important.

In alternative forms the present invention provides a catheter lock infusion device. The infusion device comprises a syringe containing a lock solution prepared according to the present invention. In yet another form the present invention also includes a kit for accessing a patient's intravascular system. The kit includes a catheter having at least one lumen. A container of a catheter lock solution that was prepared according to the present invention is included in the kit. In one embodiment the lock solution includes a viscosifying agent dissolved or dispersed in the lock solution.

For the purpose of promoting further understanding and appreciation of the present invention and its advantages, the following Example is provided. It will be understood, however, that this Example is illustrative and not limiting in any fashion.

Example Illustrating Use of Lock Solutions Containing Citrate Salts

Methods

A study utilizing concentrated citrate in the catheter lock solution was performed on an outpatient dialysis unit (RTC) with 60% of patients having chronic central venous catheters (50 catheters total, the majority ASH SPILTCATH and the remaining TESIO and HICKMAN catheters). At four-month intervals, the citrate concentration in the lock solution was increased from 10% to 20% to 47%. Gentamicin was added at 3 mg/ml to the 10% and the 20% solutions, but not to the 47% citrate solution. The overall incidence of bacteremia in the unit was followed and the amount of urokinase used to open occluded or low-flowing catheters was recorded. The results were compared in incidences of bacteremia and use of urokinase in the unit before the implementation of the lock solution containing citrate salts.

Starting in 1994, all episodes of bacteremia in the outpatient hemodialysis unit were monitored and recorded. Episodes were totaled each month, for all patients, for patients with and without tunneled central venous catheters, and for patients with and without catheter-related explanations for bacteremia. The incidence of bacteremia was calculated as the percent of patients in the unit developing bacteremia per month ("1%"=1 bacteremic episode per 100 patients in the unit for one month, or 3.3 episodes per 1000 patient-months). The incidence was graphed each month, for the entire period since 1994.

During the period from January 1998 to July 1999, there were 70 patients in this unit, with approximately 60% having tunneled central venous catheters for chronic dialysis (40 catheters total). At the start of the study, the most prevalent catheter in the unit was the Medcomp twin TESIO, though there were a few Bard SOFT CELL catheters. Starting in January 1998, the Medcomp ASH SPLITCATH catheter became the standard tunneled catheter placed in patients beginning dialysis or needing catheter replacement. Almost all of these tunneled catheters were placed using the SITE-RITE ultrasound device for IJ localization. These catheters routinely provided an average blood flow near 300 ml/min.

The average monthly incidence of positive blood cultures in the unit was calculated for the time period from January 1998 through July 1998. During this time period, heparin was used as the standard catheter lock solution, with either 5,000 units or 10,000 units instilled into each lumen at exactly the catheter volume. The incidence of bacteremia during this period was 4.6%, which was higher than the average level since 1994. In August 1998, hemodialysis patients were informed of the plan to change from heparin to sodium citrate/gentamicin as the standard anticoagulant lock for tunneled catheters. From September to December 1998, 10% citrate with 3 mg/ml gentamicin was used as standard catheter lock, injecting slightly more than the catheter volume (2.5 ml total). From January 1999 through April 1999, 20% citrate with 3 mg/ml gentamicin was the standard catheter lock, injecting slightly more than the catheter volume (2.5 ml total). From May 1999 to July 1999, 47% citrate was the standard catheter lock, injecting exactly the catheter volume. All citrate solutions were made from 47% stock solution, used straight from the 30 ml bottle or in combination with saline and gentamicin. (46.7% trisodium citrate, "triCitrasol", Citra Anticoagulants, Inc., distributed by Ash Medical Systems, West Lafayette, Ind.). Patients were closely monitored for any evidence of adverse reactions each time the citrate concentration was increased. The monthly incidence of bacteremia was calculated for the 10-month period during which citrate/gentamicin or 47% citrate was used for catheter lock, and compared to the baseline 7-month period by Two-tailed T Test (assuming equal variances).

Also during this time period, the unit use of urokinase (Abbott Laboratories) was monitored. The number of vials of urokinase use by the RTC unit was calculated on a monthly basis. The total number of vials ordered and used by the unit each month in the period from January 1998 through July 1998 was compared to the number of vials used after the conversion to citrate, from September 1998 to July 1999. After May 1999, urokinase became unavailable, but before this time it was available on request. The number of vials used per month in the baseline period was compared to the number of vials after implementation of citrate/gentamicin or 47% citrate catheter lock, by Two-tailed T Test (assuming equal variances).

During the study period, the longevity of tunneled catheters was also investigated, since the prevention of infection of tunneled catheters is less important if other factors such as clotting or sheath formation limit the life of the catheters. All Ash SPLITCATH catheters placed in end-stage renal disease (ESRD) patients after January 1998 (including patients in two satellite outpatient units) were evaluated and the longevity of the catheters was determined. In all, 57 Splitcath catheters were placed in 57 patients. Failure was defined as any catheter being removed for any complication, whether due to infection or obstruction of flow. Longevity of catheters was determined using lifetable analysis.

Since the outpatient unit has many patients with tunneled catheters, nurses and technicians use utmost care in opening the catheters and connecting to dialysis machines. The caps of the catheter are soaked in betadine for 5 minutes before the caps are removed. Nurses and technicians wear masks and gloves, and the patient wears a mask when the catheter is opened. New protective caps are placed on the catheter following each procedure. Catheters and connectors are inspected for leaks or evidence of damage, each treatment.

Incidence of Bacteremia

Figure 2:
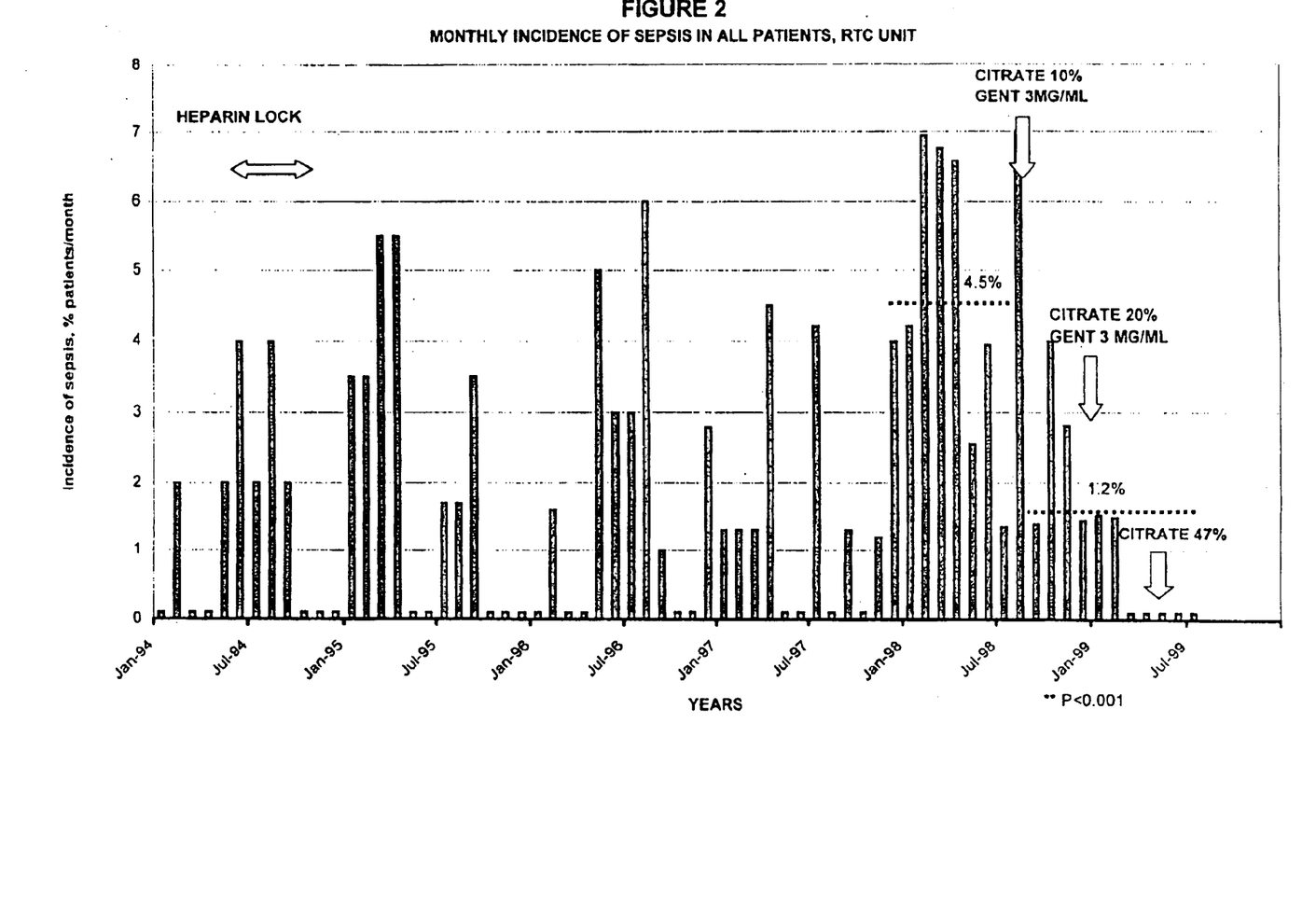
FIG. 2 is a graph plotting monthly incidence of sepsis in all patients of a hemodialysis unit.

The incidence of bacteremia in all 70 patients at the RTC unit was 4.5% of patients per month during the baseline period from January through July of 1998. Following the implementation of hypertonic citrate/gentamicin and then 47% citrate as catheter lock, the incidence of bacteremia decreased significantly to 1.2% (FIG. 2, P<0.001). There was a downward trend in bacteremia as concentration of citrate was increased from 10 to 20 to 47%. In the last three months of the study, when 47% citrate was used, the incidence of bacteremia has been zero.

Utilization of Urokinase

Figure 3:
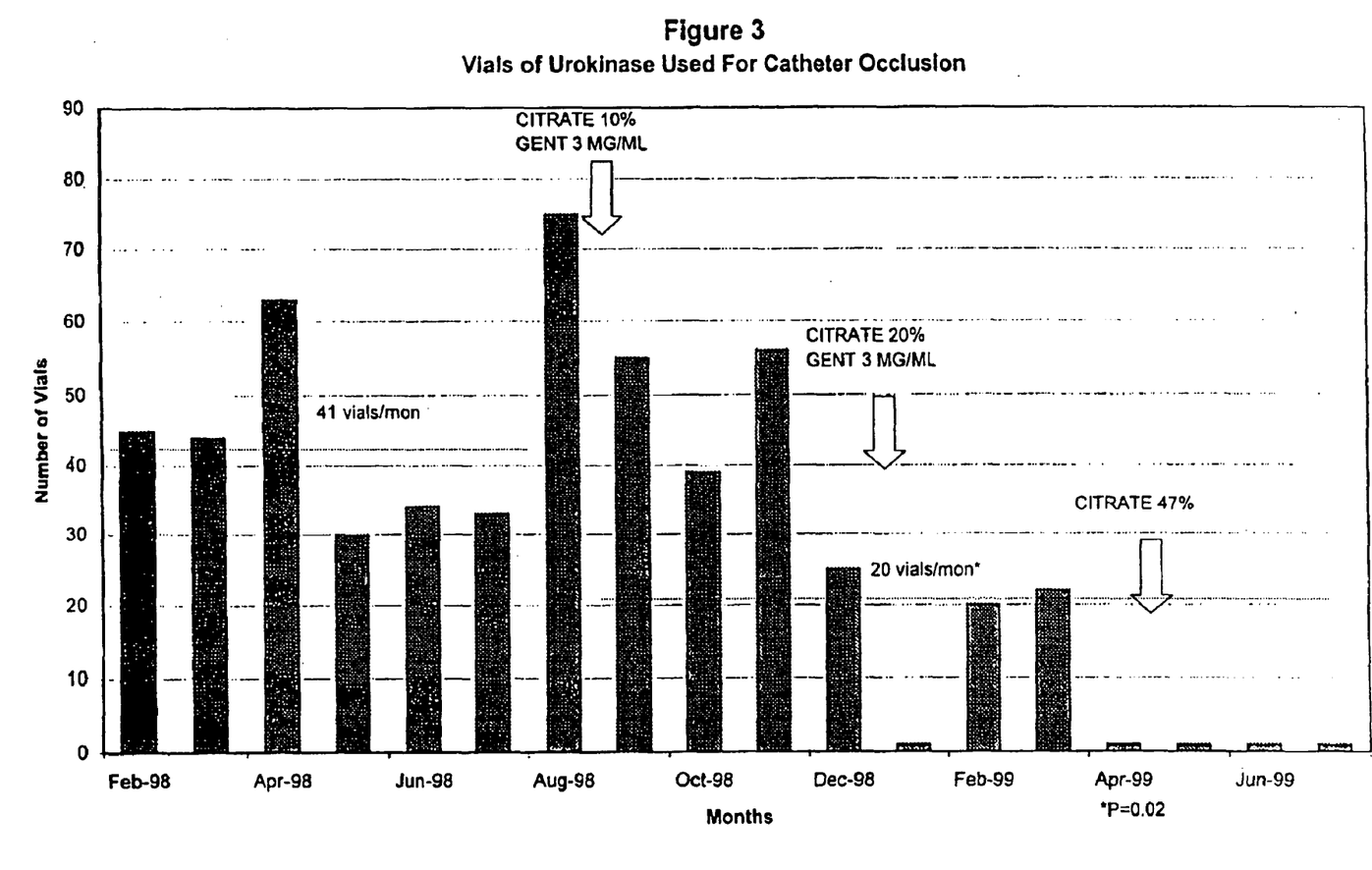
FIG. 3 is a graph plotting the number of vials of urokinase used for catheter occlusion per month in a hemodialysis hospital unit.

The use of urokinase in the dialysis unit during the baseline period was 41 vials per month, or approximately 1 vial per patient with tunneled catheter per month. After implementation of hypertonic citrate/gentamicin then 47% citrate as catheter lock, the use of urokinase decreased to 20 vials per month, about vial per patient with tunneled catheter per month (FIG. 3, P=0.02). During the last three months of this study (May, June, July 1999), no urokinase was used for any catheter. In June and July of 1999, urokinase was unavailable at the hospital, and the hospital had not yet substituted syringes of tissue plasminogen activator (tPA) for catheter infusion. However, no catheters were completely occluded or removed for flow problems during these months, so it did not appear that urokinase was required in this month.

Catheter Survival

Figure 4:
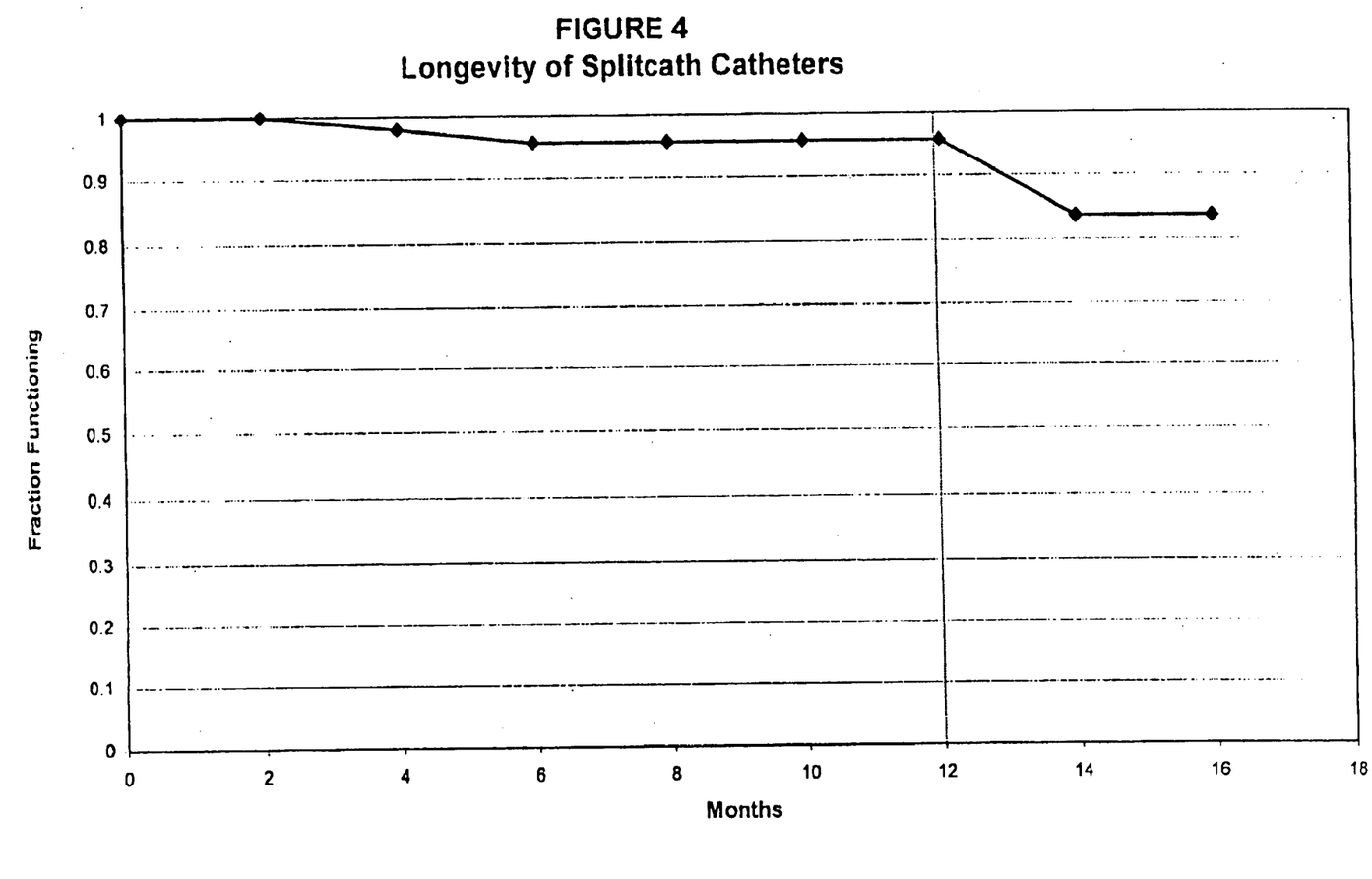
FIG. 4 is a graph plotting the longevity of one embodiment of a tunnel catheter for use with the present invention.

During the period from January 1998 to July 1999, 57 ASH SPLITCATH catheters were placed in 57 patients in the RTC and satellite units, with an average follow-up of 8 months. One small satellite unit continued using heparin for anticoagulant catheter lock, while the other followed the RTC protocol of increasing citrate catheter lock concentration. During this period, catheters without signs of infection were not removed for bacteremia, but only in patients in whom antibiotic therapy failed to clear signs of infection within 24 hours. Only 3 of the 57 catheters were removed, 2 for concomitant infection which failed to clear, and one for decreased blood outflow rate. The lifetable analysis of longevity of these catheters indicates a 95% survival at one year (FIG. 4). Interventions in these catheters were few, and as discussed above, urokinase use was decreased as hypertonic citrate/gentamicin or 47% citrate were used as catheter lock. Mean catheter flow rate for the Splitcath® catheter remained approximately 300 ml/min during the study, with venous and arterial pressures below 250 mmHg (the predefined limit for pressures in these dialysis units).

Conclusions/Discussion

In this study of tunneled catheters in a single dialysis unit, hypertonic citrate (10 or 20%) in combination with gentamicin, or 47% citrate are at least as effective as heparin in preventing clotting of the catheters. The use of urokinase to open these tunneled catheters does not increase, and in fact significantly decreases after implementation of the citrate catheter lock solutions.

Hypertonic citrate as catheter lock appears to decrease the incidence of bacteremia in a dialysis unit with a high percentage of patients with tunneled catheters. When catheters are locked with 10% or 20% citrate containing 3 mg/ml gentamicin, the incidence of bacteremia decreases significantly. An even greater decrease in incidence of bacteremia appears to occur with use of 47% citrate alone (without gentamicin). Through a variety of actions, concentrated citrate is bactericidal and sporicidal when tested in vitro. Therefore, it is expected that it would diminish the bacterial content of catheters after chance contamination of the catheter hub. On the other hand, a similar antibacterial effect could be obtained through the effect of citrate on biofilm; if the mild corrosive action of citrate helps to eliminate the biofilm, it would also eliminate bacteria trapped within the biofilm. The effect of citrate on bacterial contamination of catheters can decrease risk of bacteremia in patients with catheters without the risk of developing resistant strains of the bacteria (as will occur with antibiotic lock solutions).

Of course, with proper care it is possible to utilize tunneled catheters for dialysis without an antibacterial solution infused. In a satellite outpatient hospital dialysis unit, 20 stable ESRD patients are dialyzed, and the percentage and types of catheters (60% of patients, mostly having mostly SPLITCATH catheters and some TESIO catheters) are similar to those at the RTC unit. The unit uses the same precautions as the RTC unit in handling tunneled catheters. As opposed to the RTC, this unit has traditionally had a very low to zero incidence of bacteremia from any cause. In the period of January 1998 to May 1999, this unit continued to use heparin as catheter lock solution, and had only one patient with bacteremia during this period (representing 5% of all patients, for one month). For all other months the incidence of bacteremia remained zero. Urokinase use also remained low during the entire period.

The problems of infection and occlusion of tunneled catheters for dialysis are paralleled by the smaller catheters used in hospitalized patients with central venous catheters, and in home patients with long-term. TPN, chemotherapeutic and antibiotic administrations. Concentrated citrate may also provide significant advantages in these patients, avoiding catheter clotting, infection and subsequent bacteremia.

The present invention contemplates modification to the infusion device and method of treating patients as would occur to those skilled in the art. It is also contemplated that processes embodied in the present invention can be altered, rearranged, substituted, deleted, duplicated, combined, or added to other processes as would occur to those skilled in the art without departing from the spirit of the present invention. In addition, the various stages, procedures, techniques, phases, and operations within these processes may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. A method for treating a patient, comprising:
selecting a patient having an indwelling intravascular catheter defining a lumen therethrough and having an infection or a substantial risk of infection related to the presence of the catheter; and
infusing a catheter lock solution into the lumen, the solution comprising a citrate salt solution having a concentration effective to eliminate infection and to reduce the likelihood of subsequent infection;
wherein the lock solution comprises a citrate salt in a concentration range, in weight percent, of between about 10% and about 40%.

2. The method of claim 1 wherein the catheter has an internal volume and said infusing includes injecting the catheter with an amount of the lock solution greater than or equal to about 1.1 times the internal volume of the lumen.

3. The method of claim 1 wherein the lumen of the catheter has an internal volume and said infusing includes infusing the lumen with an amount of the lock solution sufficient to fill between about 80% and about 100% of the internal volume of the lumen.

4. The method of claim 1 wherein the lock solution comprises a citrate salt in a concentration range, in weight percent, of between about 20% and about 30%.

5. The method of claim 1 wherein the lock solution includes a viscosifying agent.

6. The method of claim 1 wherein the lock solution has a pH level between about 4.5 and about 6.5.

7. The method of claim 5 wherein the viscosifying agent is selected from polyethylene glycol, glycerin, polygeline and mixtures thereof.

8. A method of inhibiting infections in an animal having an indwelling catheter defining at least one lumen therethrough, said method comprising infusing into the lumen a pharmaceutically acceptable lock solution including a compound having anticoagulant and antibiotic activity, wherein said lock solution has a density of between about 1.0 g/ml and about 1.5 g/ml and a viscosity of between about 1.5 cP and about 4.0 cP.

9. The method of claim 8 wherein the animal is a human.

10. The method of claim 8 wherein the lock solution includes a citrate salt in a hypertonic concentration range, in weight percent, of between 1.5% and 50%.

11. The method of claim 10 wherein the lock solution includes a citrate salt in a concentration range, in weight percent, of between 10% and 40%.

12. The method of claim 11 wherein the lock solution includes a citrate salt in a concentration range, in weight percent, of between 20% and 30%.

13. The method of claim 8 wherein the lock solution includes a viscosifying agent.

14. The method of claim 8 wherein the lock solution has a density of between about 1.02 g/ml to about 1.04 g/ml and a viscosity of between about 1.5 cP and about 4.0 cP.

15. The method of claim 8 wherein the lock solution has a density of between about 1.02 g/ml and about 1.03 g/ml and a viscosity of between about 1.5 cP and about 2.0 cP.

16. The method of claim 8 wherein the lumen of the catheter has an internal volume and said infusing includes infusing the lumen with an amount of the lock solution sufficient to fill between about 80% and about 100% of the internal volume of the lumen.

17. The method of claim 8 wherein the lumen of the catheter has an internal volume and said infusing includes infusing the lumen with an amount of the lock solution greater than or equal to about 1.1 times the internal volume of the lumen.

18. The method of claim 8 wherein the lock solution has a pH level between about 4.5 and about 6.5.

19. A method of treating animals having a surgically implanted catheter, said method comprising infusing into said catheter a pharmaceutically acceptable lock solution comprising a bactericidal component, said bactericidal component including greater than about 50%, by weight based on the weight of the bactericidal component, of a citrate salt.

20. The method of claim 19 wherein the bactericidal component includes greater than about 75%, by weight based on the weight of the bactericidal component, of a citrate salt.

21. The method of claim 19 wherein the bactericidal component includes greater than about 90%, by weight based on the weight of the bactericidal component, of a citrate salt.

22. The method of claim 19 wherein the lock solution includes a viscosifying agent.

23. The method of claim 19 wherein the pharmaceutically acceptable lock solution has a pH between about 4.5 and about 6.5.

24. The method of claim 19 wherein the lumen of the catheter has an internal volume and said infusing includes infusing the lumen with an amount of the lock solution sufficient to fill between about 80% and about 100% of the internal volume of the lumen.

25. The method of claim 19 wherein the lumen of the catheter has an internal volume and said infusing includes infusing the lumen with an amount of the lock solution greater than or equal to about 1.1 times the internal volume of the lumen.

26. The method of claim 19 wherein the animal is a human.

27. The method of claim 19 wherein the bactericidal component consists essentially of sodium citrate dissolved in the solution.

28. The method of claim 19 wherein said catheter lock solution is essentially free from any therapeutically effective concentration of any other bactericidal compound other than sodium citrate.

29. A method for treating a patient, comprising:
  selecting a patient having an indwelling intravascular catheter defining a lumen therethrough, and needing a bactericidal catheter lock solution; and
  infusing a catheter lock solution into the lumen, the solution comprising a bactericidal component;
  wherein the bactericidal component consists essentially of sodium citrate dissolved in the solution.

30. A method for treating a patient, comprising:
  selecting a patient that has an indwelling intravascular catheter defining a lumen therethrough and that has a need for infusion of a bactericidal catheter lock solution into the lumen of the catheter; and
  responding to the need by infusing into the lumen a catheter lock solution comprising a citrate salt solution having a concentration effective to eliminate infection and to reduce the likelihood of subsequent infection.

31. The method of claim 30 wherein the catheter lock solution comprises a bactericidal component, and wherein the bactericidal component consists essentially of sodium citrate dissolved in the solution.

32. The method of claim 30 wherein the lock solution has a density of between about 1.0 g/ml and about 1.5 g/ml and a viscosity of between about 1.5 cP and about 4.0 cP.

33. The method of claim 30 wherein the lock solution has a density of between about 1.02 g/ml and about 1.04 g/ml and a viscosity of between about 1.5 cP and about 4.0 cP.

34. The method of claim 30 wherein the lock solution includes a citrate salt having a concentration, in weight percent, of from about 1.5% to about 50%.

35. The method of claim 13 wherein the viscosifying agent is selected from polyethylene glycol, glycerin, polygeline and mixtures thereof.

* * * * *